(12) United States Patent
Field et al.

(10) Patent No.: US 10,497,550 B1
(45) Date of Patent: Dec. 3, 2019

(54) SYSTEMS AND METHODS FOR HOT PLASMA ANALYSIS OF ANALYTES USING MEMBRANE DESOLVATOR

(71) Applicant: Elemental Scientific, Inc., Omaha, NE (US)

(72) Inventors: Michael Paul Field, Papillion, NE (US); Jordan Krahn, Omaha, NE (US)

(73) Assignee: ELEMENTAL SCIENTIFIC, INC., Omaha, NE (US)

( * ) Notice: Subject to any disclaimer, the term of this patent is extended or adjusted under 35 U.S.C. 154(b) by 0 days.

(21) Appl. No.: 16/011,691

(22) Filed: Jun. 19, 2018

Related U.S. Application Data

(60) Provisional application No. 62/523,533, filed on Jun. 22, 2017.

(51) Int. Cl.
| | | |
|---|---|---|
| *H01J 49/10* | (2006.01) | |
| *H01J 49/26* | (2006.01) | |
| *H01J 49/04* | (2006.01) | |
| *G01N 21/73* | (2006.01) | |
| *G01J 3/443* | (2006.01) | |
| *G01J 3/02* | (2006.01) | |

(52) U.S. Cl.
CPC ......... *H01J 49/0445* (2013.01); *G01J 3/0267* (2013.01); *G01J 3/443* (2013.01); *G01N 21/73* (2013.01); *H01J 49/0422* (2013.01); *H01J 49/0477* (2013.01); *H01J 49/105* (2013.01)

(58) Field of Classification Search
CPC ............... H01J 49/0445; H01J 49/0422; H01J 49/0477; H01J 49/105; G01J 3/0267; G01J 3/443; G01N 21/73
USPC ................................. 250/423 R, 428, 288
See application file for complete search history.

(56) References Cited

U.S. PATENT DOCUMENTS

| | | | |
|---|---|---|---|
| 6,864,974 B1 | 3/2005 | Wiederin et al. | |
| 8,695,813 B2 * | 4/2014 | Carson | B01D 1/0094 210/149 |
| 2010/0181387 A1 * | 7/2010 | Zaffaroni | A61M 15/06 239/13 |
| 2013/0004798 A1 * | 1/2013 | Huang | H01M 8/16 429/2 |

* cited by examiner

*Primary Examiner* — Nicole M Ippolito
(74) *Attorney, Agent, or Firm* — Kevin E. West; Advent, LLP

(57) ABSTRACT

Systems and methods for measuring analytes (e.g., potassium) under hot plasma conditions of ICP analysis systems (e.g., ICP-MS, ICP-AES, etc.) are described, where a membrane desolvation unit and nitrogen flow gas are included to reduce Argon interferences. A system embodiment includes a heated spray chamber configured to receive a liquid sample and a sample gas to aerosolize the liquid sample; a first condenser coupled to the heated spray chamber; a second condenser coupled to the first condenser; a heated membrane coupled to the second condenser; and a gas introduction component coupled to the heated membrane to receive a flow of gas and to combine the flow of gas with a dried sample aerosol leaving the heated membrane, wherein the flow of gas is introduced at a rate of approximately 2.67 percent to approximately 20 percent of a flow rate of the sample gas.

20 Claims, 16 Drawing Sheets

SYSTEMS AND METHODS FOR HOT PLASMA ANALYSIS OF ANALYTES USING MEMBRANE DESOLVATOR

CROSS-REFERENCE TO RELATED APPLICATIONS

The present application claims the benefit of 35 U.S.C. § 119(e) of U.S. Provisional Application Ser. No. 62/523,533, filed Jun. 22, 2017, and titled "SYSTEMS AND METHODS FOR HOT PLASMA ANALYSIS OF ANALYTES USING MEMBRANE DESOLVATOR." U.S. Provisional Application Ser. No. 62/523,533 is herein incorporated by reference in its entirety.

BACKGROUND

Spectrometry refers to the measurement of radiation intensity as a function of wavelength to identify component parts of materials. Inductively Coupled Plasma (ICP) spectrometry is an analysis technique commonly used for the determination of trace element concentrations and isotope ratios in liquid samples. For example, in the semiconductor industry, ICP spectrometry can be used to determine metal concentrations in samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample. The sample to be analyzed is often provided in a sample mixture.

Sample introduction systems may be employed to introduce liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

Systems and methods for measuring analytes (e.g., potassium) under hot plasma conditions of ICP analysis systems (e.g., ICP-MS, ICP-AES, etc.) are described, where a membrane desolvation unit and nitrogen flow gas are included to reduce argon (Ar) interferences. A system embodiment includes a heated spray chamber configured to receive a liquid sample and a sample gas to aerosolize the liquid sample; a first condenser coupled to the heated spray chamber; a second condenser coupled to the first condenser; a heated membrane coupled to the second condenser; and a gas introduction component coupled to the heated membrane to receive a flow of gas and to combine the flow of gas with a dried sample aerosol leaving the heated membrane, wherein the flow of gas is introduced at a rate of approximately 2.67 percent to approximately 20 percent of a flow rate of the sample gas.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. In the figures, the use of the same reference numbers in different instances in the description and the figures may indicate similar or identical items.

FIG. 3A is a cross-sectional view of a flow gas introduction component for the system shown in FIG. 1 in accordance with example implementations of the present disclosure.

FIG. 3B is a cross-sectional view of a flow gas introduction component for the system shown in FIG. 1 in accordance with example implementations of the present disclosure.

DETAILED DESCRIPTION

Overview

For quantitative analysis of many elements, such as potassium, argon can inhibit the accuracy of such analyses by providing an interfering mass of particular counts measured by a sample analysis system (e.g., ICP-MS, ICP-AES, etc.). For instance, argon is often used as a plasma gas in ICP analysis systems, which under hot plasma conditions (e.g., approximately 1200 W and higher) can generate substantial amounts of ionized argon. The ionized argon can react with hydrogen (e.g., from moisture presented to the plasma) to form argon hydride (ArH) or the like to interfere with analysis of potassium, its ions and isotopes, or other analytes. Argon hydride can pose a significant interference for the analysis of components with a mass of 41 (e.g., potassium isotope $^{41}K$) or ratios thereof (e.g., $^{39}K/^{41}K$) due to the abundance of argon present for ionization under traditional hot plasma conditions. The amount of argon interference can be reduced by operating the ICP analysis system under cool plasma conditions (e.g., approximately 750 W and below) to provide less power to the plasma, thus generating fewer argon ions available for reaction with hydrogen. However, operation of the cool plasma conditions can inhibit the capability of maintaining the plasma for a suitable time period for substantial sample analyses.

Accordingly, the present disclosure is directed to systems and methods for reducing the interference of argon using a sample preparation system under hot plasma conditions, where the system includes a membrane desolvator to dry the sample aerosol and a nitrogen flow gas introduced to the dry sample aerosol prior to introduction to an ICP analysis system operating under hot plasma conditions. The membrane desolvator can remove water and other solvents prior to ionization in the plasma, thereby removing sources of hydrogen from interacting with the argon plasma gas. The presence of the added nitrogen in the sample flow can further act a barrier to interaction between argon and hydrogen, thereby reducing the likelihood of argon hydride formation, while avoiding introducing interferences for potassium and potassium isotopes.

Example Implementations

Figure 1:
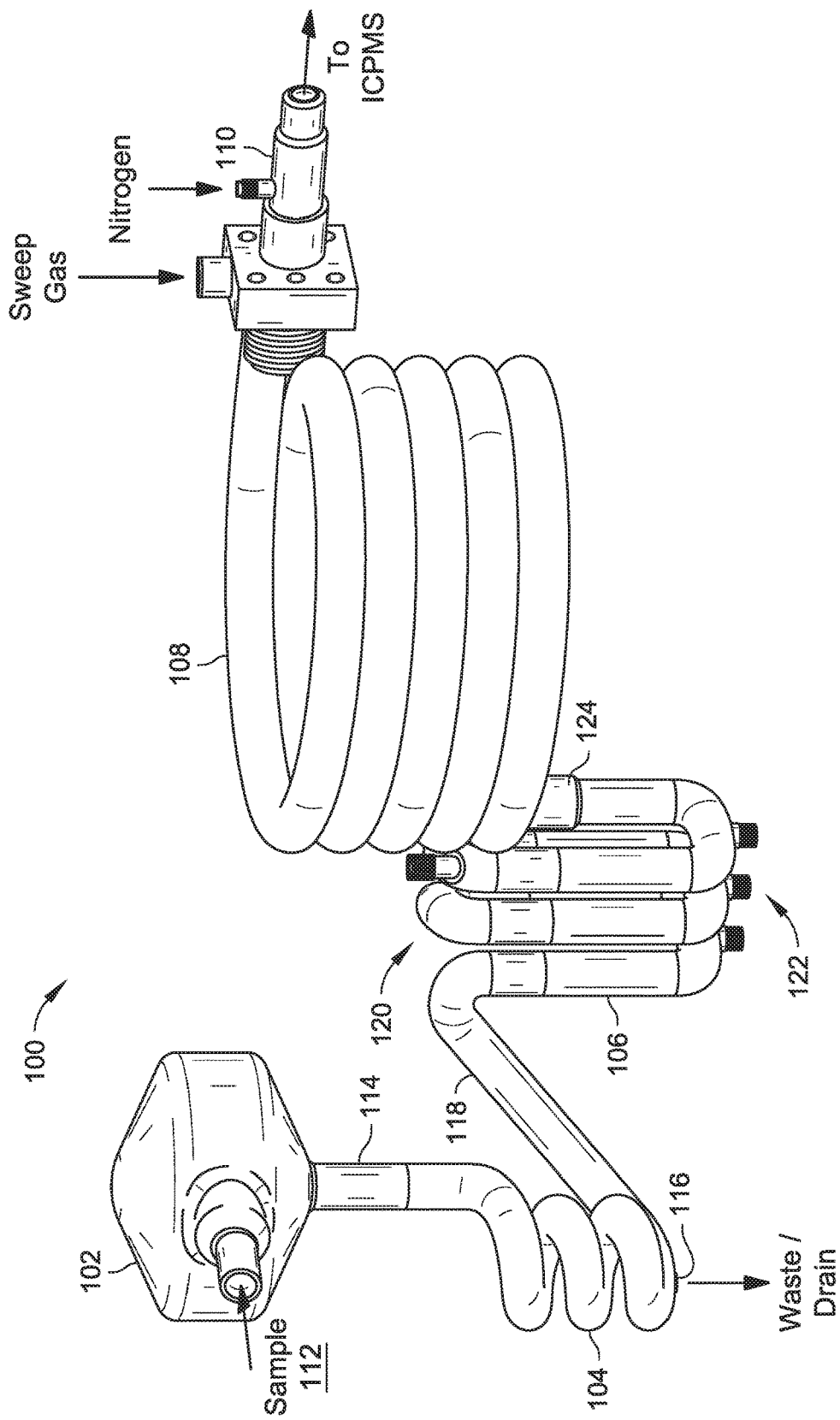
FIG. 1 is a schematic illustration of a system for preparation of a sample for analysis by ICP spectrometry instrumentation in accordance with example implementations of the present disclosure.
Figure 2:
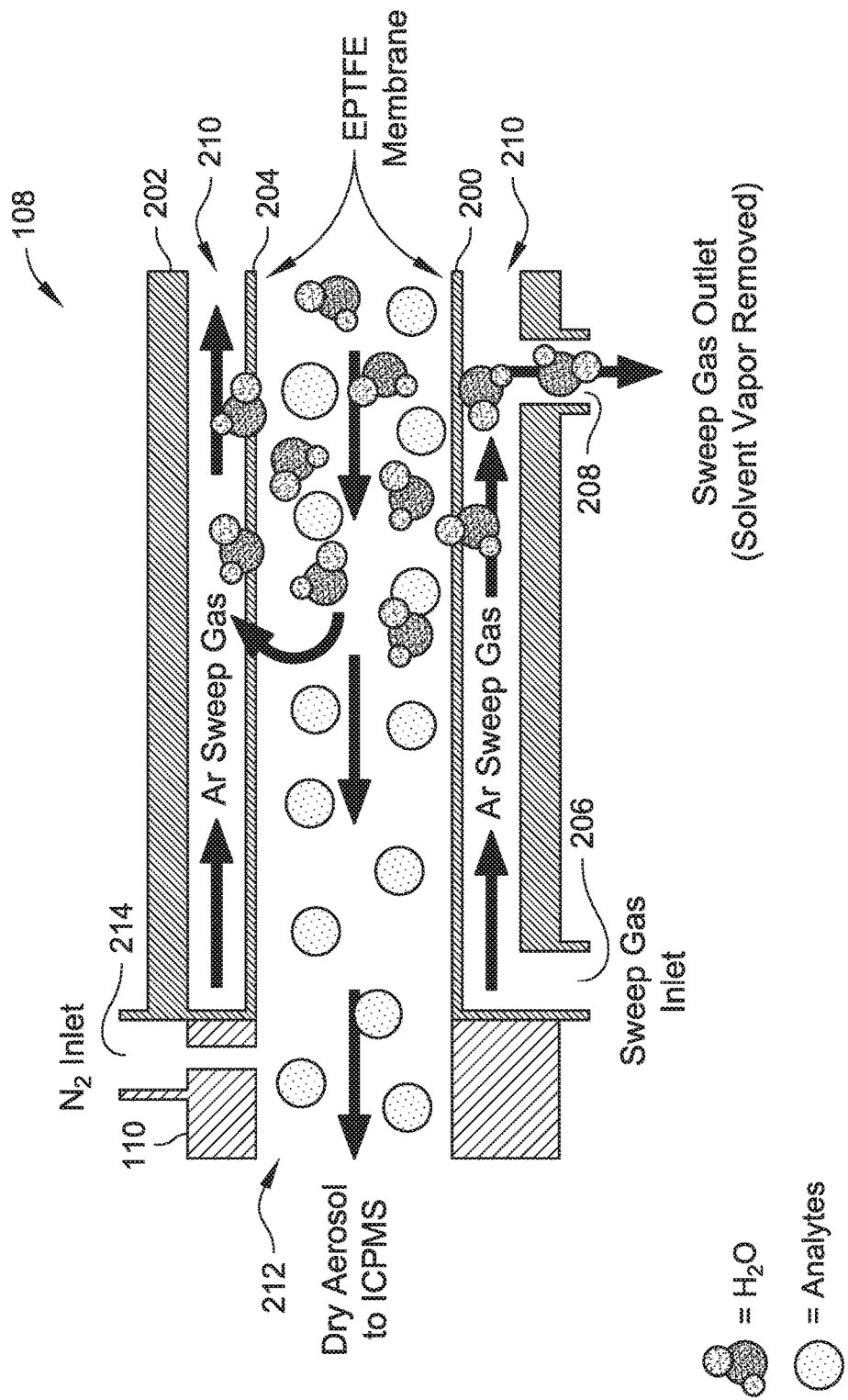
FIG. 2 is a schematic illustration of a cross-section of a membrane desolvation unit for the system shown in FIG. 1 in accordance with example implementations of the present disclosure.
Figure 4A:
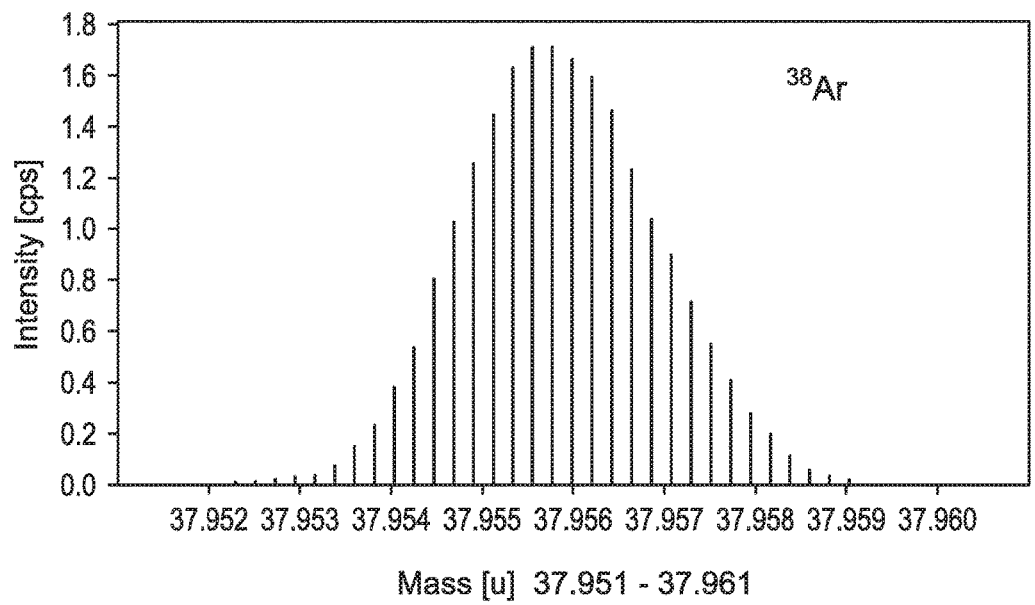
FIG. 4A is a chart of intensity versus mass as a result of analysis of a 10 parts per billion (ppb) potassium solution with a sample preparation employing a cyclonic spray chamber and hot plasma analysis conditions.
Figure 4B:
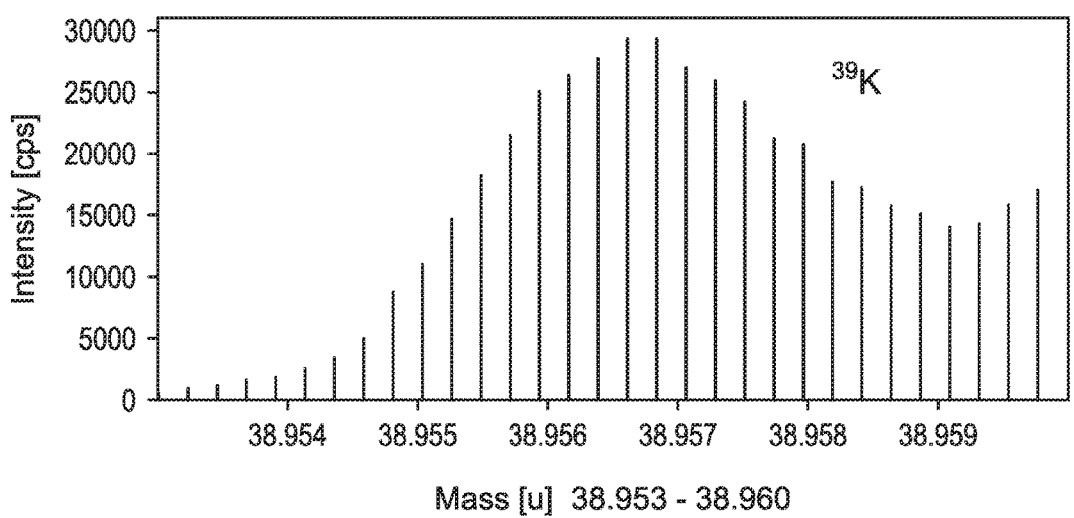
FIG. 4B is a chart of intensity versus mass as a result of analysis of a 10 parts per billion (ppb) potassium solution with a sample preparation employing a cyclonic spray chamber and hot plasma analysis conditions.
Figure 4C:
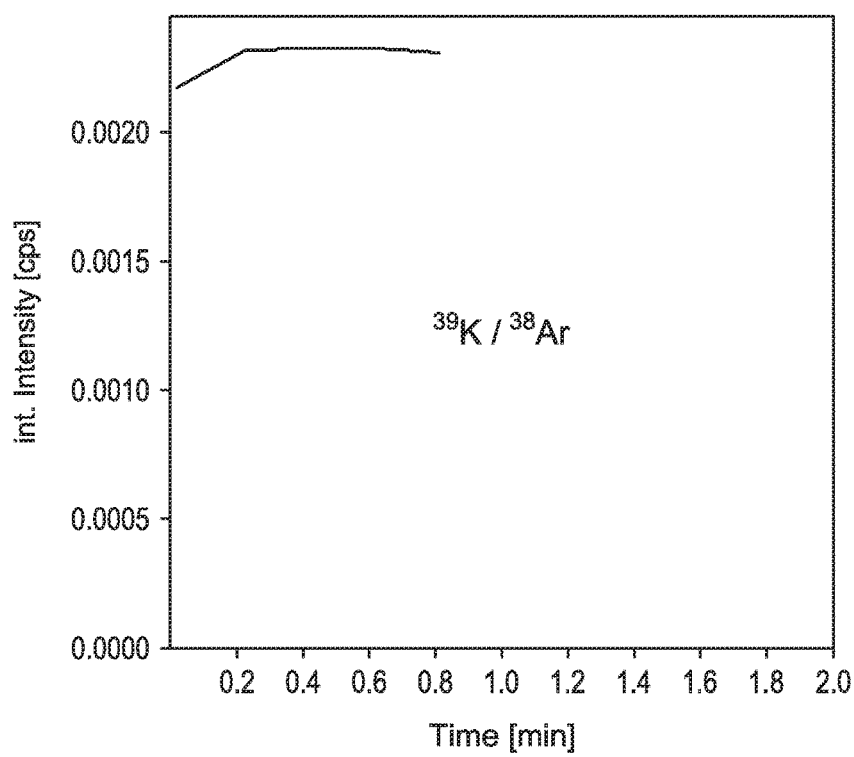
FIG. 4C is a chart of intensity versus time as a result of analysis of a 10 parts per billion (ppb) potassium solution with a sample preparation employing a cyclonic spray chamber and hot plasma analysis conditions.
Figure 4D:
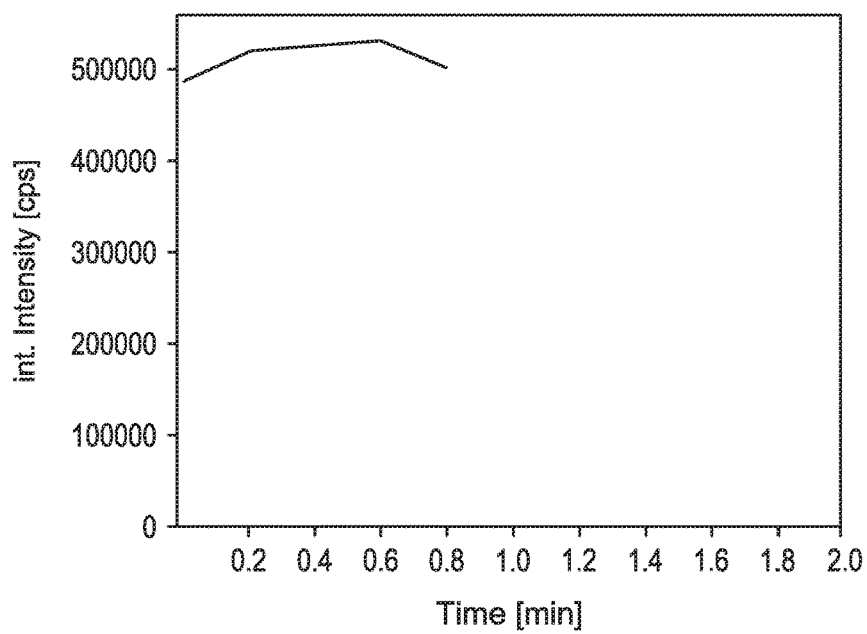
FIG. 4D is a chart of intensity versus time as a result of analysis of a 10 parts per billion (ppb) potassium solution with a sample preparation employing a cyclonic spray chamber and hot plasma analysis conditions.
Figure 4E:
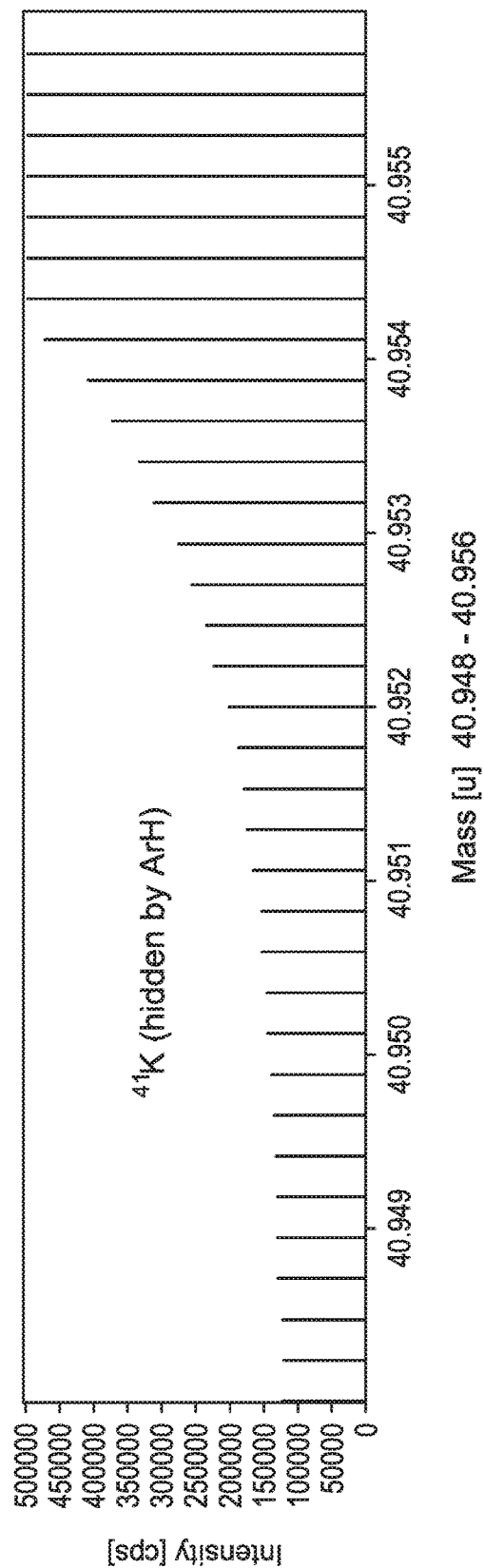
FIG. 4E is a chart of intensity versus mass as a result of analysis of a 10 parts per billion (ppb) potassium solution with a sample preparation employing a cyclonic spray chamber and hot plasma analysis conditions.
Figure 4F:
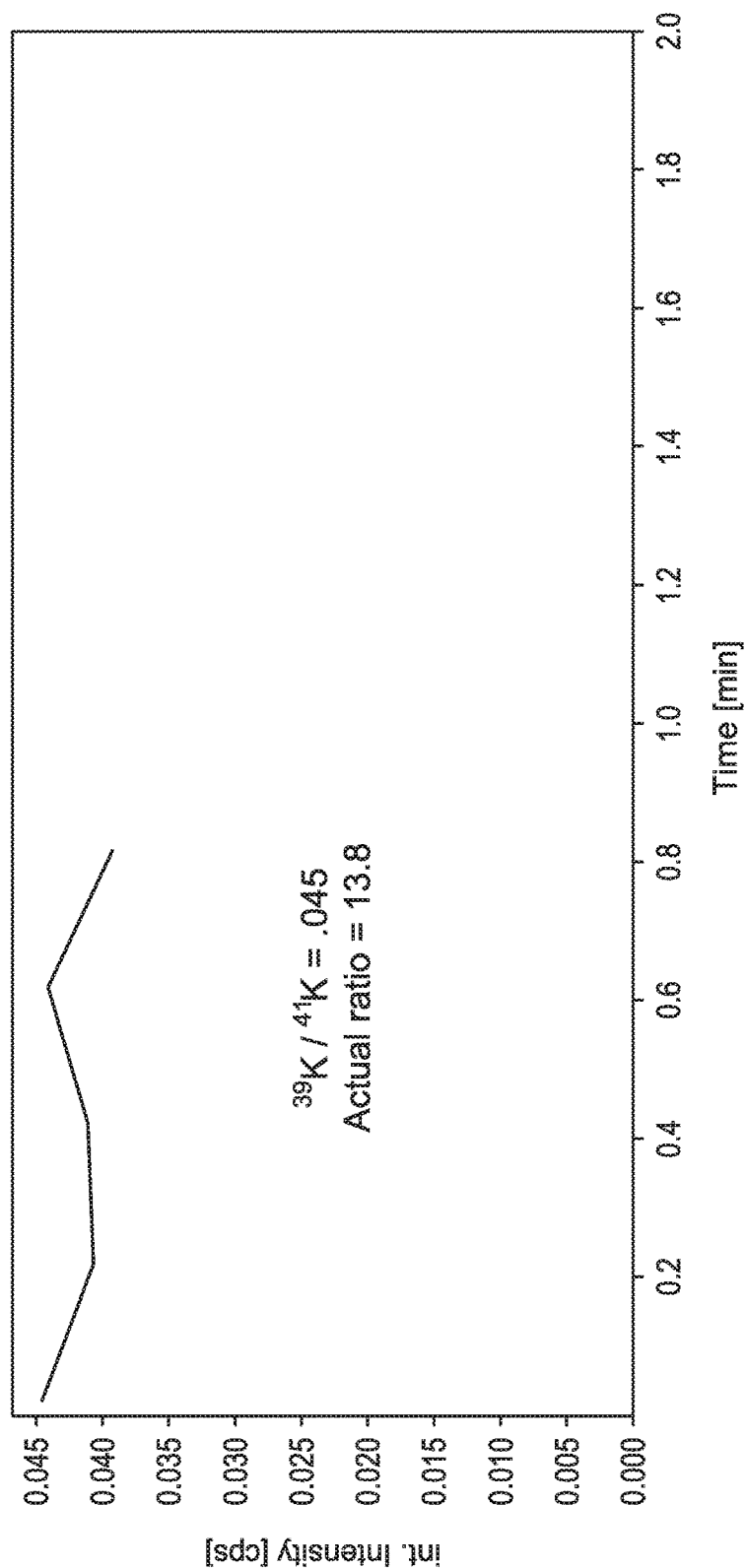
FIG. 4F is a chart of intensity versus time as a result of analysis of a 10 parts per billion (ppb) potassium solution with a sample preparation employing a cyclonic spray chamber and hot plasma analysis conditions.
Figure 5A:
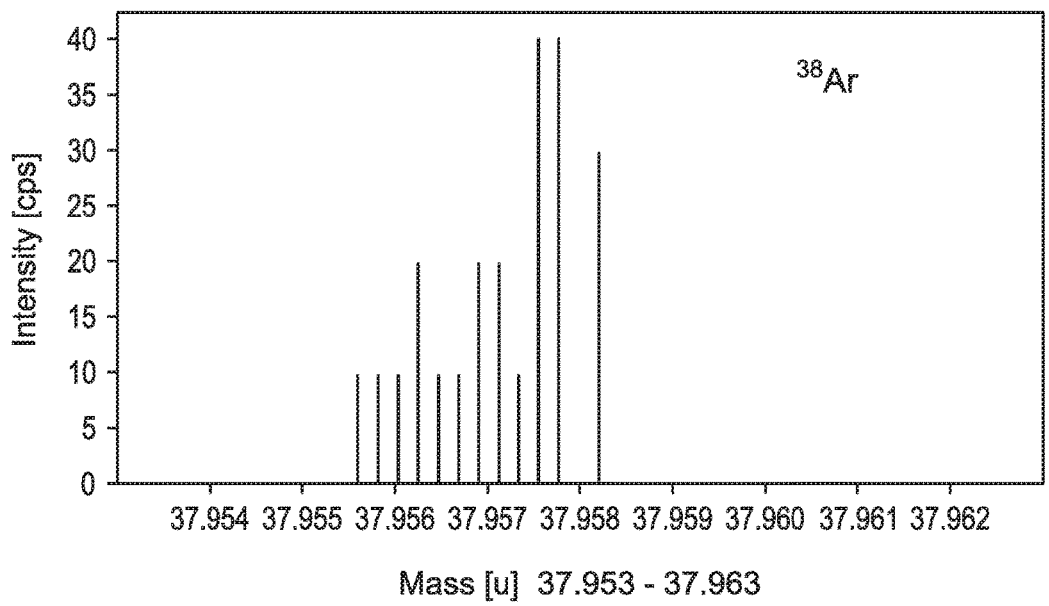
FIG. 5A is a chart of intensity versus mass as a result of analysis of a blank solution with the sample preparation system of FIG. 1 having a nitrogen flow gas introduced to the dry sample aerosol in accordance with example implementations of the present disclosure.
Figure 5B:
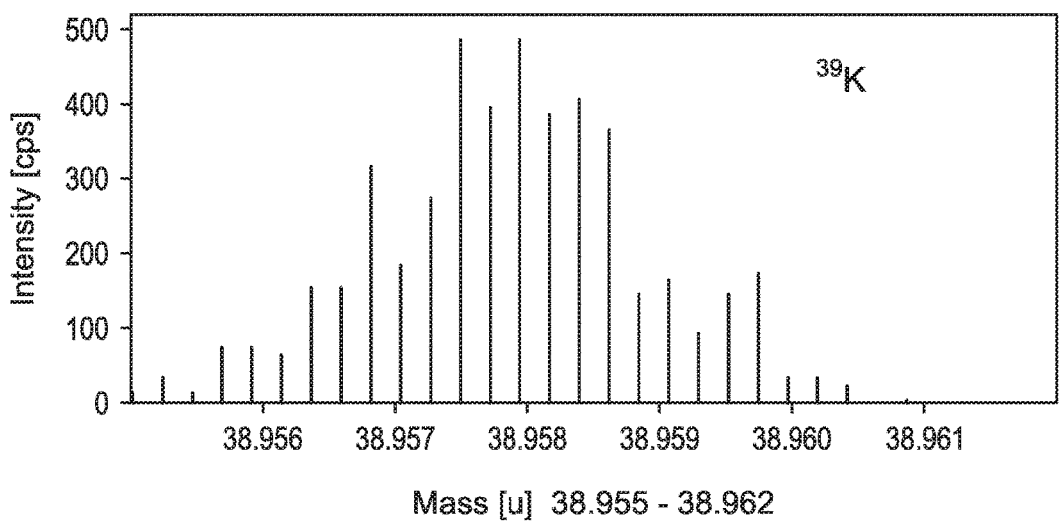
FIG. 5B is a chart of intensity versus mass as a result of analysis of a blank solution with the sample preparation system of FIG. 1 having a nitrogen flow gas introduced to the dry sample aerosol in accordance with example implementations of the present disclosure.
Figure 5C:
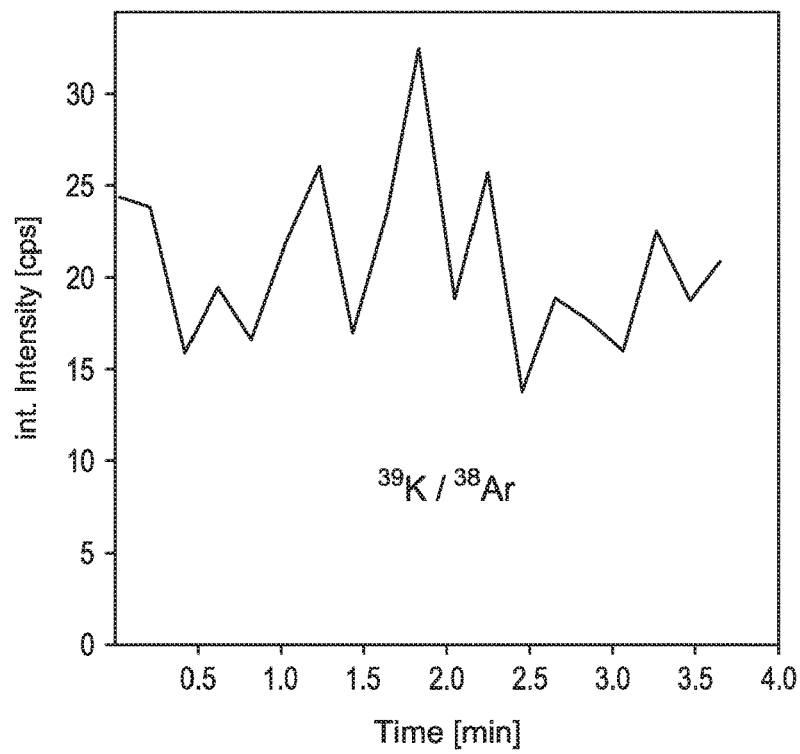
FIG. 5C is a chart of intensity versus time as a result of analysis of a blank solution with the sample preparation system of FIG. 1 having a nitrogen flow gas introduced to the dry sample aerosol in accordance with example implementations of the present disclosure.
Figure 5D:
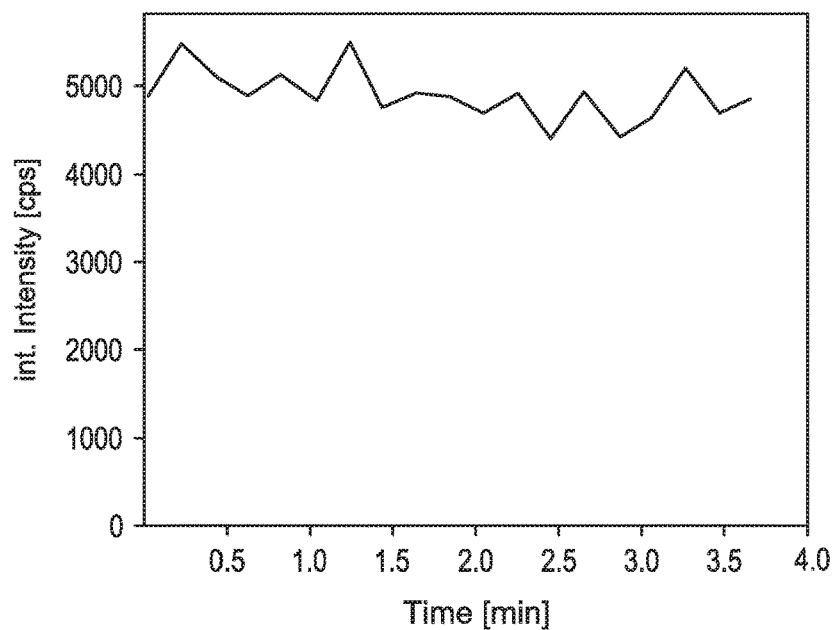
FIG. 5D is a chart of intensity versus time as a result of analysis of a blank solution with the sample preparation system of FIG. 1 having a nitrogen flow gas introduced to the dry sample aerosol in accordance with example implementations of the present disclosure.
Figure 5E:
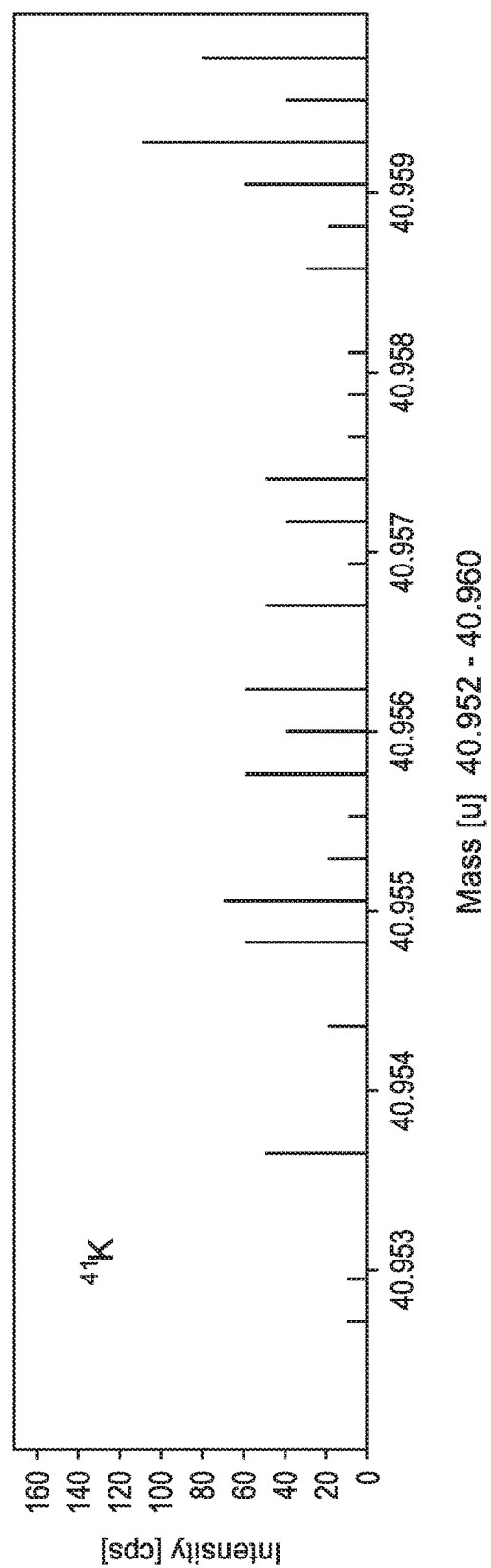
FIG. 5E is a chart of intensity versus mass as a result of analysis of a blank solution with the sample preparation system of FIG. 1 having a nitrogen flow gas introduced to the dry sample aerosol in accordance with example implementations of the present disclosure.
Figure 5F:
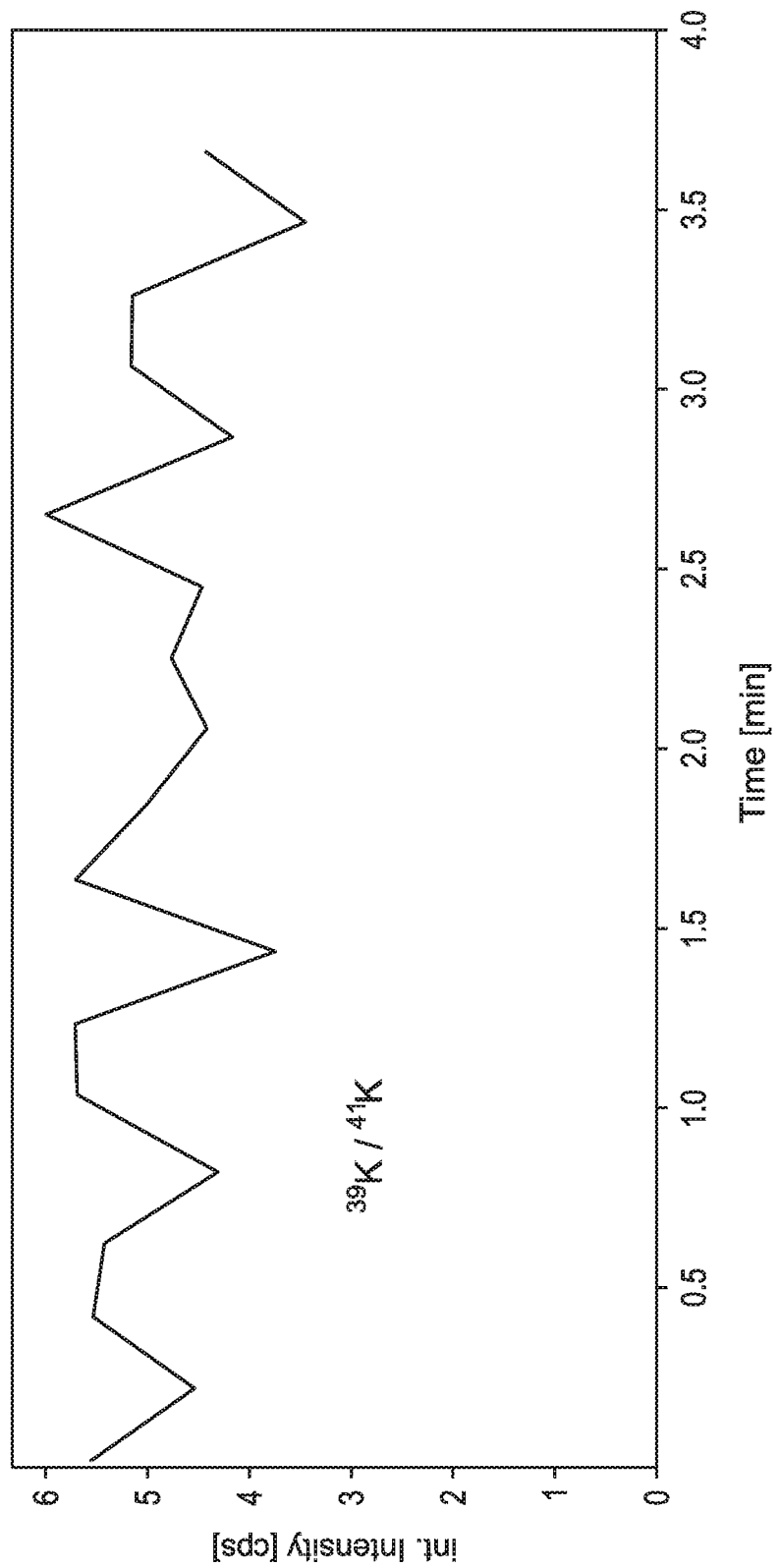
FIG. 5F is a chart of intensity versus time as a result of analysis of a blank solution with the sample preparation system of FIG. 1 having a nitrogen flow gas introduced to the dry sample aerosol in accordance with example implementations of the present disclosure.
Figure 6A:
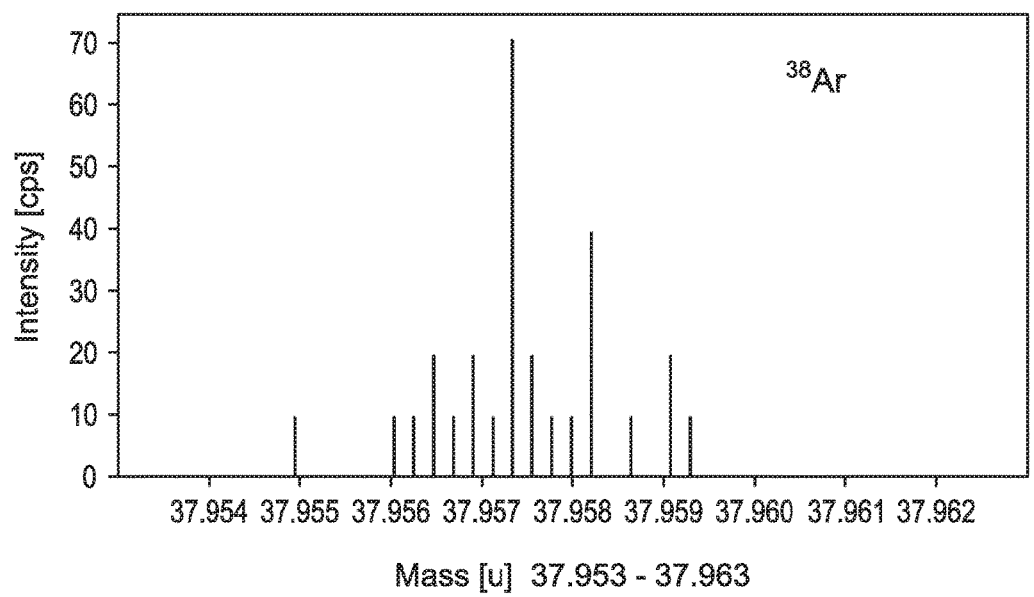
FIG. 6A is a chart of intensity versus mass as a result of analysis of a 10 parts per billion (ppb) potassium solution under hot plasma conditions with the sample preparation system of FIG. 1 having a nitrogen flow gas introduced to the dry sample aerosol in accordance with example implementations of the present disclosure.
Figure 6B:
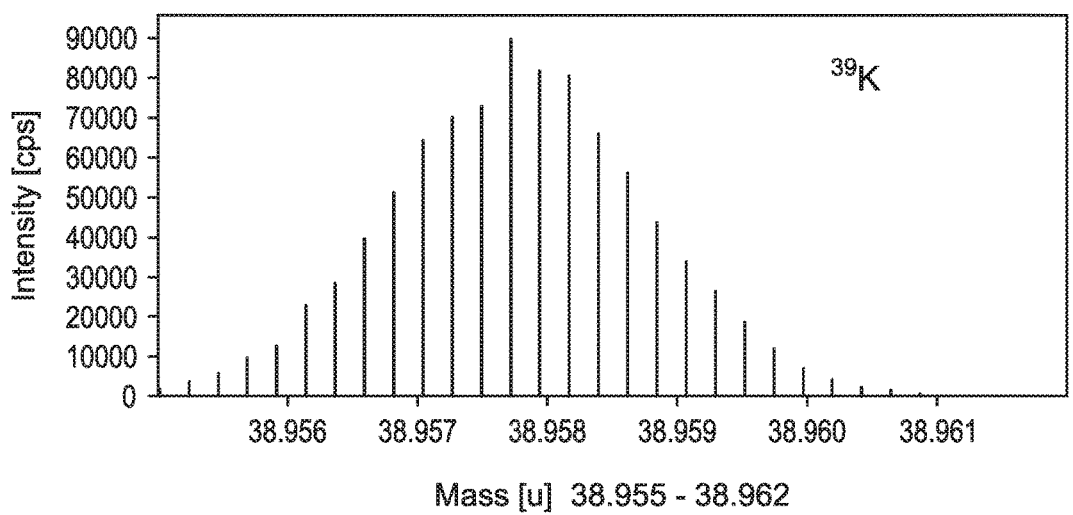
FIG. 6B is a chart of intensity versus mass as a result of analysis of a 10 parts per billion (ppb) potassium solution under hot plasma conditions with the sample preparation system of FIG. 1 having a nitrogen flow gas introduced to the dry sample aerosol in accordance with example implementations of the present disclosure.
Figure 6C:
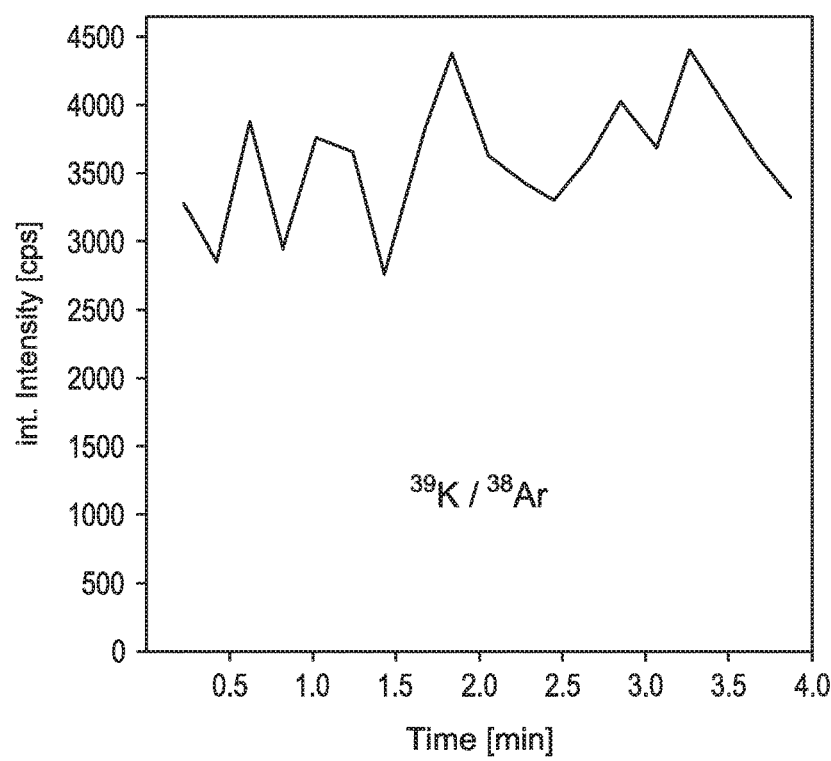
FIG. 6C is a chart of intensity versus time as a result of analysis of a 10 parts per billion (ppb) potassium solution under hot plasma conditions with the sample preparation system of FIG. 1 having a nitrogen flow gas introduced to the dry sample aerosol in accordance with example implementations of the present disclosure.
Figure 6D:
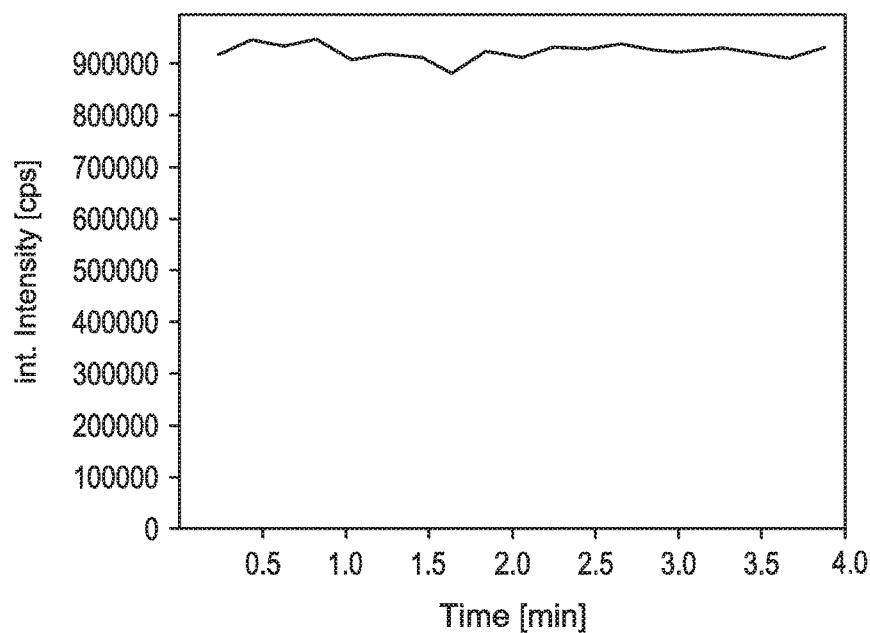
FIG. 6D is a chart of intensity versus time as a result of analysis of a 10 parts per billion (ppb) potassium solution under hot plasma conditions with the sample preparation system of FIG. 1 having a nitrogen flow gas introduced to the dry sample aerosol in accordance with example implementations of the present disclosure.
Figure 6E:
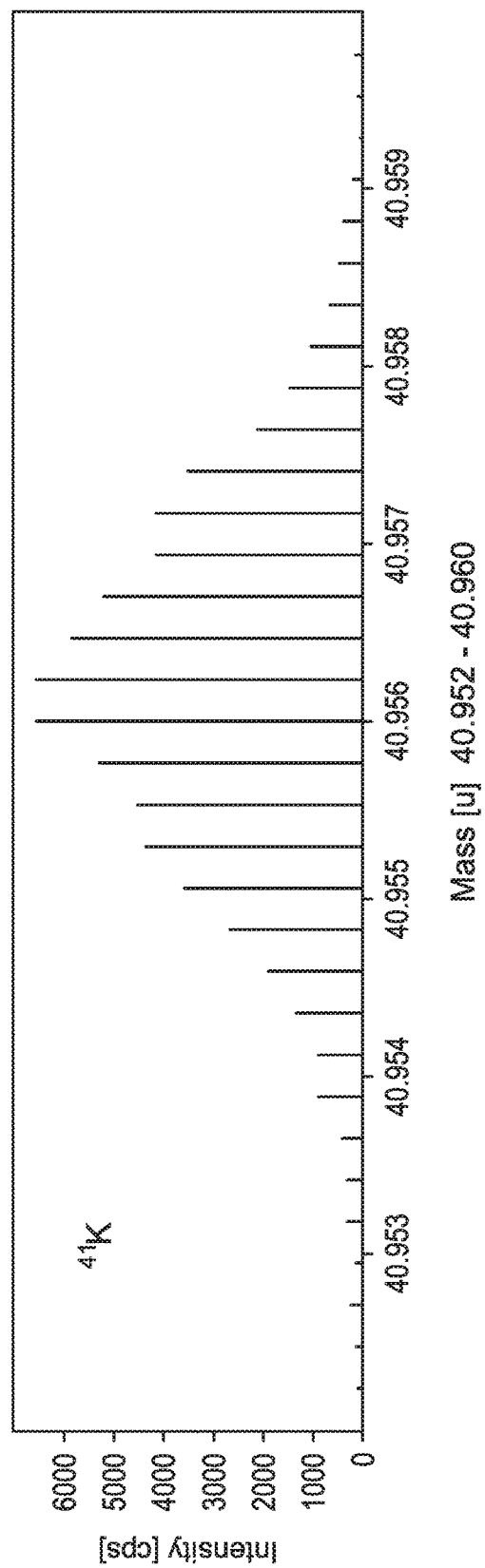
FIG. 6E is a chart of intensity versus mass as a result of analysis of a 10 parts per billion (ppb) potassium solution under hot plasma conditions with the sample preparation system of FIG. 1 having a nitrogen flow gas introduced to the dry sample aerosol in accordance with example implementations of the present disclosure.
Figure 6F:
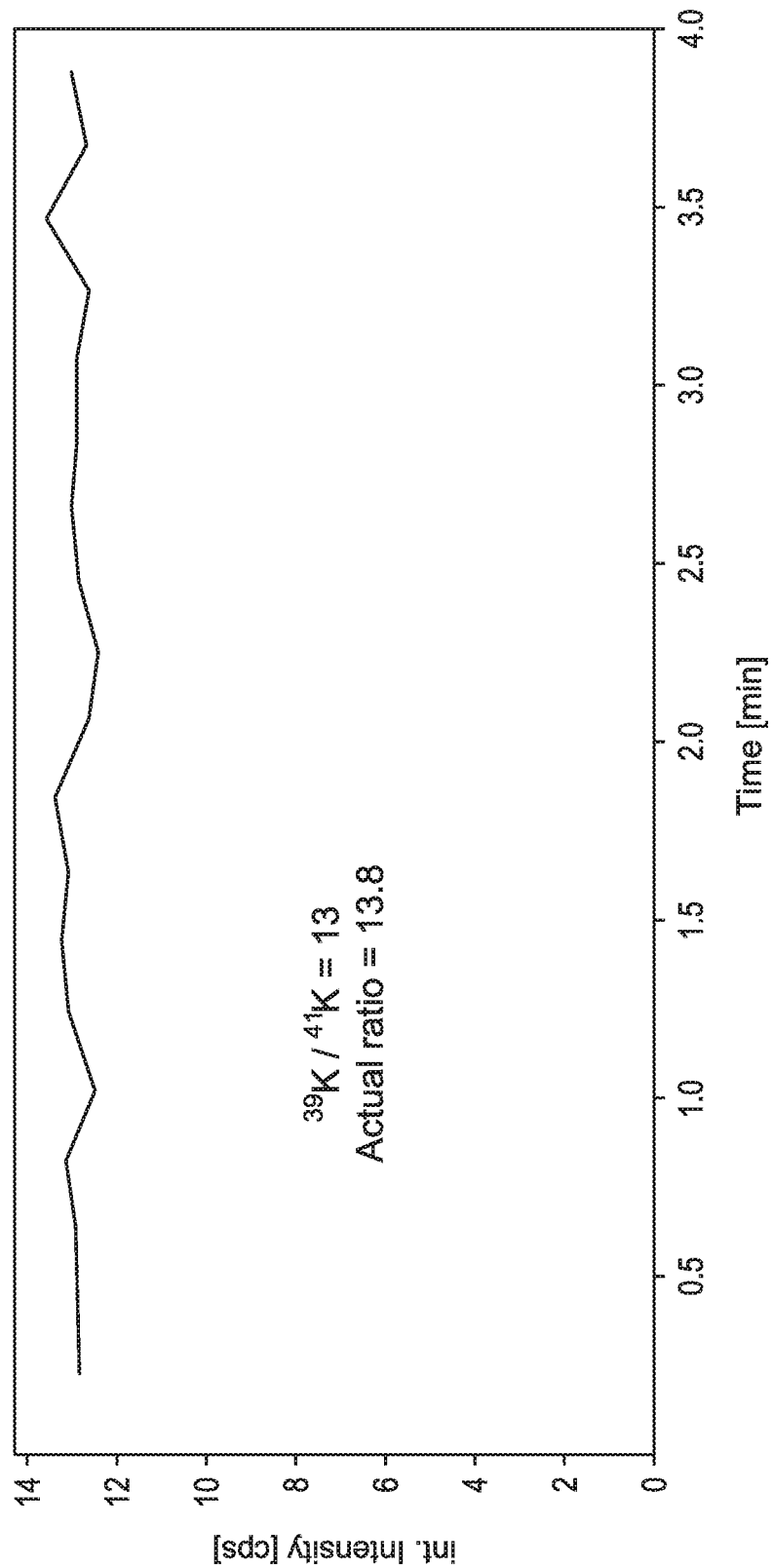
FIG. 6F is a chart of intensity versus time as a result of analysis of a 10 parts per billion (ppb) potassium solution under hot plasma conditions with the sample preparation system of FIG. 1 having a nitrogen flow gas introduced to the dry sample aerosol in accordance with example implementations of the present disclosure.

Referring generally to FIGS. 1 and 2, systems are shown to prepare a sample for analysis by an ICP analysis system under hot plasma conditions (e.g., approximately 1200 W and higher) while reducing the interference of argon for the analysis of potassium (e.g., potassium ions, potassium isotopes, potassium isotopic ratios, etc.). In an implementation, shown in FIG. 1, a system 100 includes a heated spray chamber 102, a first condenser 104, a second condenser 106, a heated membrane 108, and a flow gas introduction component 110. A sample 112 is introduced to the heated spray chamber 102, such as via a nebulizer with nebulizing gas to aerosolize the sample 112 prior to introduction to the heated spray chamber 102. In an implementation, the heated spray chamber 102 is maintained at a temperature above the boiling point of the sample 112 to evaporate liquid solvent in the aerosolized sample 112, such as where the heated spray chamber 102 is heated to a temperature above ambient conditions. The aerosolized sample 112 including the evaporated solvent can pass out of the heated spray chamber 102 via outlet 114 into the first condenser 104. The evaporated solvent can condense into liquid within the first condenser 104 and exit the system 100 via a drain 116 positioned in a bottom portion of the first condenser 104, where the aerosolized sample 112 can continue into the second condenser 106 via outlet 118. In an implementation, the second condenser 106 includes a plurality of loops 120 that alternatively cool and warm the aerosol, such as by maintaining a temperature gradient from warm to cool at the upper region of each loop to the lower region of each loop to further condense solvent present in the aerosolized sample 112. In an implementation, the second condenser 106 includes a thermoelectric cooling unit, a Peltier cooler, another cooling unit, or combinations thereof to maintain the temperature gradient from warm to cool at the upper region of each loop to the lower region of each loop. The condensed solvent can be removed from the second condenser 106 via one or more drains 122. The aerosolized sample 112 can continue into the heated membrane 108 via outlet 124. In an implementation, the heated membrane 108 is maintained at a temperature above the boiling point of the sample 112 to evaporate liquid solvent in the aerosolized sample 112, such as where the heated membrane 108 is heated to a temperature above ambient conditions. In an implementation, the heated membrane 108 includes concentric tubes separated by a membrane permeable to the solvent. A sweep gas (e.g., Ar) flows in the annular portion to remove solvent that has transferred from the inner tube to the outer tube by crossing the membrane.

An implementation of the heated membrane 108 is shown in FIG. 2, where the heated membrane 108 includes a concentric arrangement of an inner tube 200 and an outer tube 202 separated by a membrane 204 (e.g., an expanded polytetrafluoroethylene (EPTFE) membrane). In an implementation, the membrane 204 is permeable to the solvent (e.g., water) but not substantially permeable to the analytes of interest (e.g., potassium and/or other metallic ions). In an implementation, at least a portion of the inner tube 200 is formed of the membrane 204 within the outer tube 202. For example, the membrane 204 can include a tubular shape that forms the inner tube 200 within the outer tube 202. The heated membrane 108 can include a sweep gas inlet 206 and a sweep gas outlet 208 coupled to an annular region 210 between the inner tube 200 and the outer tube 202 to carry solvent through the annular region 210 and out of the heated membrane 108 via the sweep gas outlet 208. The flow gas introduction component 110 is coupled to an outlet end 212 of the heated membrane 108 to receive the dried aerosol and to introduce a flow gas (e.g., nitrogen ($N_2$)) to the dried aerosol via a flow gas inlet 214 prior to introduction to the ICP analysis system. Example implementations of the flow gas introduction component are described with reference to FIGS. 3A and 3B herein. The flow rate of the flow gas introduced to the flow gas inlet 214 can depend on the flow rate of the amount of sample flowing through the heated membrane 108 or on the flow rate of the amount of sample initially introduced to the heated spray chamber 102. In implementations, the flow rate of the flow gas (e.g., $N_2$) introduced to the flow gas inlet 214 is from approximately 40 mL/min to approximately 100 mL/min for sample gas flow rates from approximately 0.5 L/min to approximately 1.5 L/min (i.e., the flow rate of gas (e.g., argon) introduced to the heated spray chamber 102 via nebulizer), and for sample uptake flow rates from approximately 20 µL/min to approximately 300 µL/min (i.e., the flow rate of liquid sample nebulized prior to introduction to the heated spray chamber 102). For example, in an implementation, the flow rate of the flow gas introduced to the flow gas inlet 214 is from approximately 60 mL/min to approximately 70 mL/min for sample gas flow rates from approximately 0.5 L/min to approximately 1.5 L/min, and for sample uptake flow rates from approximately 20 µL/min to approximately 300 µL/min. In implementations, the flow gas introduced to the flow gas inlet 214 (e.g., flow rate of nitrogen introduced via inlet 214) is introduced at a rate of approximately 2.67 percent to approximately 20 percent of the sample gas flow rate. As used herein, the term "approximately" is used to indicate the numeric value and functional equivalents thereof.

Figure 3A:
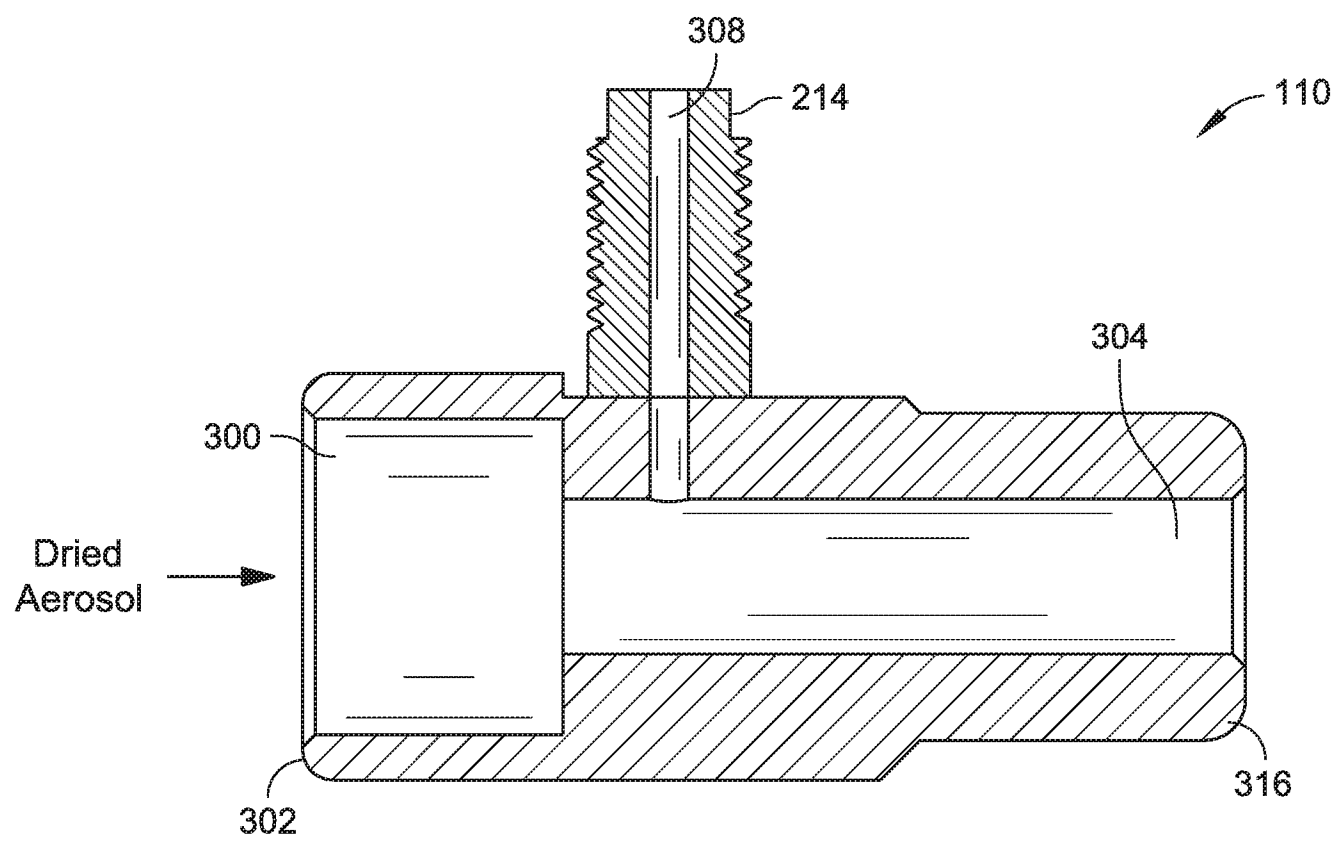

Referring to FIG. 3A, an example implementation of the flow gas introduction component 110 is shown. The flow gas introduction component 110 defines a first port 300 at a first end 302 to couple to the outlet end 212 of the heated membrane 108 to receive the dried aerosol from the heated membrane 108. The flow gas introduction component 110 also defines a channel 304 positioned from the first end 302 to a second end 306 of the flow gas introduction component 110 to permit passage of the dried aerosol therethrough. The flow gas inlet 214 defines a second port 308 to receive the flow gas from a flow gas source (e.g., a container of pressurized flow gas). The second port 308 is coupled to the channel 304 to introduce the flow gas to the dried aerosol as the dried aerosol travels from the first end 302 to the second end 306 of the flow gas introduction component 110. In an embodiment, the second port 308 is aligned substantially perpendicular to the channel 304, which can provide sufficient mixing of the flow gas with the dried aerosol prior to introduction to the ICP analysis system operating under hot plasma conditions. While the second port 308 is shown being aligned substantially perpendicular to the channel 304, it is contemplated that other alignment configurations of the second port 308 with respect to the channel 304 can be utilized to provide differing mixing configurations. For example, in implementations, the second port 308 is arranged at an angle from approximately 5 degrees from vertical to about 85 degrees from vertical with respect to the channel 304.

Figure 3B:
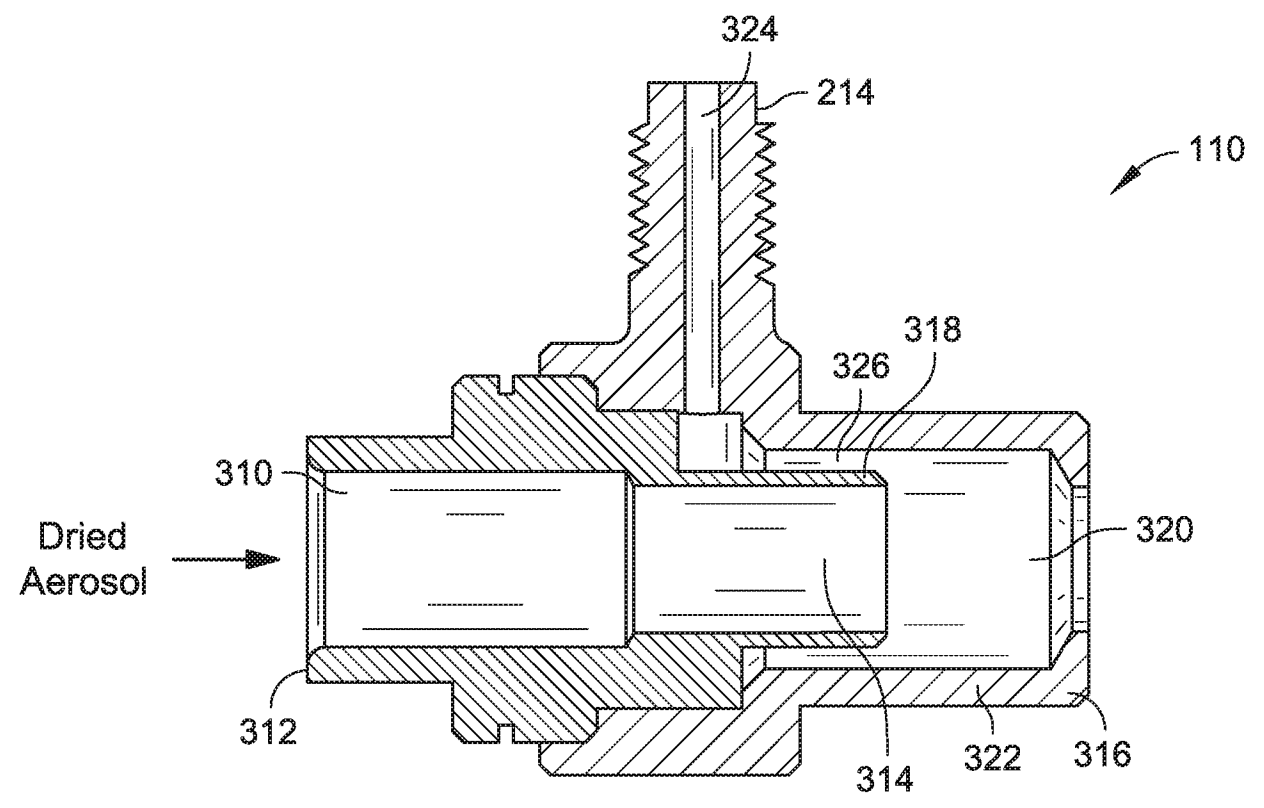

Referring to FIG. 3B, an example implementation of the flow gas introduction component 110 is shown, where the flow gas is introduced to an annular region prior to introduction to the dried aerosol. The flow gas introduction component 110 defines a first port 310 at a first end 312 to couple to the outlet end 212 of the heated membrane 108 to receive the dried aerosol from the heated membrane 108. The flow gas introduction component 110 also defines a channel 314 positioned from the first end 312 to a second end 316 of the flow gas introduction component 110 to permit passage of the dried aerosol therethrough. The channel 314 is defined in part by a first tube 318 positioned in an interior of the flow gas introduction component 110. The channel 314 opens into a mixing chamber 320 formed by a mixing chamber structure 322 of the flow gas introduction component 110 adjacent the second end 316. The flow gas inlet 214 defines a second port 324 to receive the flow gas from a flow gas source (e.g., a container of pressurized flow gas). The second port 308 is coupled to an annular portion 326 defined between an exterior surface of the first tube 318 and an interior surface of the mixing chamber structure 322 to introduce the flow gas into the annular portion 326 prior to mixing with the dried aerosol in the mixing chamber 320 as the dried aerosol travels through the channel 314 from the first end 302 to the second end 306 of the flow gas introduction component 110. In an embodiment, the flow gas spirals within the annular portion 326 to mix with the dried aerosol in the mixing chamber 320 with the dried aerosol prior to introduction to the ICP analysis system operating under hot plasma conditions.

Referring to FIGS. 4A through 4F, results of analysis of a 10 parts per billion (ppb) potassium solution with a sample preparation of a standard cyclonic spray chamber (i.e., a system without the first condenser 104, the second condenser 106, or the heated membrane 108) and hot plasma conditions (1250 W) are shown. $^{39}K$ is measured at approximately 30,000 counts per second (cps), where the right-hand side of the $^{39}K$ peak is obscured by an $^{40}Ar$ peak. Further, the analysis included an approximately 18 million $^{38}Ar$ background, a $^{39}K/^{38}Ar$ ratio of approximately 0.002, no discernable $^{41}K$ peak (>100,000 cps background of argon hydride (ArH)), and a $^{39}K/^{41}K$ ratio of approximately 0.04 (where the actual $^{39}K/^{41}K$ ratio is 13.8, resulting in a 97% error).

Referring to FIGS. 5A through 5F, results of analysis of a blank solution prepared with the system 100 and hot plasma conditions (1250 W) are shown. In particular, the backgrounds of $^{40}$Ar peak and argon hydride (ArH) are substantially eliminated as compared to the backgrounds provided with respect to FIGS. 4A through 4F.

Referring to FIGS. 6A through 6F, results of analysis of a 10 parts per billion (ppb) potassium solution prepared with the system 100 under hot plasma conditions (1250 W) are shown. $^{39}$K is measured at approximately 90,000 counts per second (cps) with a single peak (e.g., no substantial $^{40}$Ar peak). Further, the analysis included less than approximately 100 $^{38}$Ar background (as compared to approximately 18 million in FIG. 3A), a $^{39}$K/$^{38}$Ar ratio of approximately 3500 (a $10^6$ improvement as compared to FIG. 3A), a clear $^{41}$K peak (<40 cps background of argon hydride (ArH)), and a $^{39}$K/$^{41}$K ratio of approximately 13 (where the actual $^{39}$K/$^{41}$K ratio is 13.8, resulting in a 6% error).

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A system for preparing a liquid sample for analysis by an inductively-coupled analysis system comprising:
    a heated spray chamber configured to receive a liquid sample and a sample gas to aerosolize the liquid sample;
    a first condenser coupled to the heated spray chamber;
    a second condenser coupled to the first condenser;
    a heated membrane coupled to the second condenser; and
    a gas introduction component coupled to the heated membrane to receive a flow of gas and to combine the flow of gas with a dried sample aerosol leaving the heated membrane, wherein the flow of gas is introduced at a rate of approximately 2.67 percent to approximately 20 percent of a flow rate of the sample gas.

2. The system of claim 1, wherein the sample gas is argon.

3. The system of claim 1, wherein the flow of gas includes nitrogen.

4. The system of claim 1, wherein the gas introduction component defines a channel through the gas introduction component from a first end of the gas introduction component to a second end of the gas introduction component through which the dried aerosol sample passes.

5. The system of claim 4, wherein the gas introduction component defines a port coupled to the channel to introduce the flow of gas with the dried sample aerosol within the channel.

6. The system of claim 1, wherein the gas introduction component defines an annular portion coupled with a port configured to receive the flow of gas.

7. The system of claim 6, wherein the gas introduction component further defines a channel through which the dried aerosol sample passes, and wherein each of the annular portion and the channel are coupled to a mixing chamber to introduce the flow of gas and the dried aerosol sample.

8. The system of claim 1, wherein the heated membrane includes a concentric arrangement of an inner tube and an outer tube separated by a membrane.

9. The system of claim 8, wherein the membrane is substantially permeable to a solvent of the liquid sample.

10. The system of claim 8, wherein the membrane is substantially impermeable to one or more metallic ions.

11. The system of claim 8, wherein the membrane includes an expanded polytetrafluoroethylene (EPTFE) membrane.

12. A method for preparing a liquid sample for analysis by an inductively-coupled analysis system comprising:
    introducing a liquid sample and a sample gas to a heated spray chamber to produce an aerosolized sample;
    passing the aerosolized sample through at least one condenser coupled to the heated spray chamber;
    subsequent to passing the aerosolized sample through at least one condenser coupled to the heated spray chamber, introducing the aerosolized sample to a heated membrane;
    removing at least a portion of a solvent of the aerosolized sample in the heated membrane to produce a dried aerosolized sample; and
    introducing a flow of gas to the dried aerosolized sample at a rate of approximately 2.67 percent to approximately 20 percent of a flow rate of the sample gas to produce a mixed sample.

13. The method of claim 12, further comprising:
    introducing the mixed sample to an inductively coupled plasma analysis system operating under hot plasma conditions.

14. The method of claim 12, wherein the sample gas is argon.

15. The method of claim 12, wherein the flow of gas includes nitrogen.

16. The method of claim 12, wherein the liquid sample includes potassium ions.

17. The method of claim 12, wherein introducing a liquid sample and a sample gas to a heated spray chamber to produce an aerosolized sample includes introducing the liquid sample to the heated spray chamber at a flow rate of approximately 20 µL/min to approximately 300 µL/min.

18. The method of claim 12, wherein introducing a flow of gas to the dried aerosolized sample at a rate of approximately 2.67 percent to approximately 20 percent of a flow rate of the sample gas to produce a mixed sample includes introducing the flow of gas to the dried aerosolized sample at a flow rate of approximately 40 mL/min to approximately 100 mL/min.

19. The method of claim 12, wherein introducing a flow of gas to the dried aerosolized sample at a rate of approximately 2.67 percent to approximately 20 percent of a flow rate of the sample gas to produce a mixed sample includes introducing the flow of gas to a gas introduction component coupled to the heated membrane, the gas introduction component includes an annular portion coupled with a port to receive the flow of gas, wherein the gas introduction component further defines a channel through which the dried aerosolized sample passes, and wherein each of the annular portion and the channel are coupled to a mixing chamber to introduce the flow of gas and the dried aerosolized sample.

20. The method of claim 12, wherein the heated membrane includes a concentric arrangement of an inner tube and an outer tube separated by a membrane, wherein the membrane is substantially permeable to the solvent of the liquid sample and substantially impermeable to one or more metallic ions.

* * * * *